July 22, 1969 R. S. MOORE Plant Pat. 2,910
MINIATURE ROSE PLANT
Filed Sept. 22, 1967
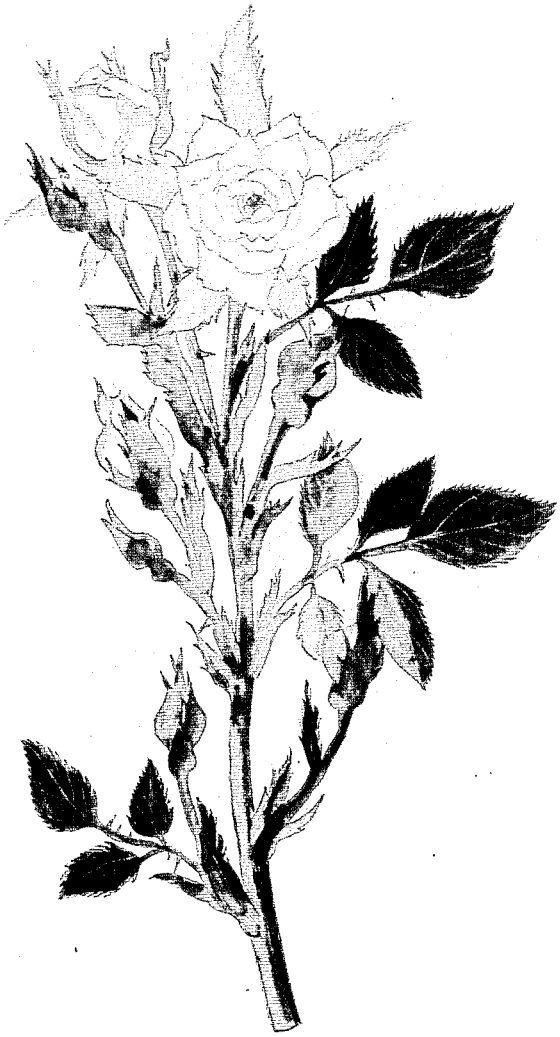
WITNESS
Jeanette Nunn Copley
INVENTOR
Ralph S. Moore United States Patent Office Plant Pat. 2,910
Patented July 22, 1969

2,910
MINIATURE ROSE PLANT

Ralph S. Moore, 2519 E. Noble Ave.,
Visalia, Calif. 93277

Filed Sept. 22, 1967, Ser. No. 669,980
Int. Cl. A01h 5/00
U.S. Cl. Plt.—7 1 Claim The present invention relates to a new and distinct variety of hardy, dwarf, semi-climbing type rose plant of the miniature class; the variety being primarily characterized, as to novelty, by flowers of a yellow and pink blending, similar to Peace (Pl. Patent 591—expired) in coloring, and the everblooming semi-climbing habit of the plant.

The variety is further characterized by:

An abundance of bloom, with flowers borne singly but most often in clusters of 3 or more to the stem. A plant which is vigorous, of bush to semi-climbing habit, with glossy, medium green leaves. The plant which has a normal average height of 15 to 30 inches at maturity, resembles the general plant habit of Pink Cameo (Pl. Patent 1,451) miniature rose, only more drawf and compact, being easily maintained in bush form; the bud and flower being similar in form to Yellow Doll (Pl. Patent 2,450) but less double.

A plant which grows and blooms satisfactorily both in the greenhouse and outdoors; is a good plant for growing in pots; and provides excellent garden decoration as well as cut flowers.

The present variety of miniature rose was originated by me in my nursery, located at Visalia, Calif., under conditions of careful control and observation, as a cross between Little Darling (a floribunda rose, U.S. Plant Patent, 1,581) as the seed parent and Zee (a miniature rose, not patented) as the pollen parent.

Subsequent to origination of the variety I successfully asexually reproduced it, in my nursery located as aforesaid, by budding as well as by cuttings; the reproductions having run true in all respects.

The figure of the drawing illustrates a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; bush/semi-climber; seedling; greenhouse; outdoors; cut flowers; garden decoration; potted plant.
Class: Miniature.
Flowers:
*Continuity.*—Continuous.
*Fragrance.*—Slight.
Flowers borne: Singly—usually in clusters of 3 or more on medium length, stiff stems.
Quantity of bloom: Abundant both outside and in greenhouse.
Bud: Peduncle—short to medium length; slender; erect; light to medium green; smooth. Before calyx breaks: size—small. Form—long, pointed; with foliaceous appendages and numerous small, short hairs on the surface of bud and foliaceous parts extending beyond the tipe of the bud equal to one half or less of its length. Color—medium green (in greenhouse), sometimes lightly tinted reddish or bronze outdoors. As calyx breaks: color—soft yellow; size—small. Form—long, pointed. Opening—opens well in all weather.
Bloom: Size when fully open—small, 1¼". Petalage: double—25 petals. Form—high centered, becoming more flat at maturity.

Petals: rather thick, stiff, satiny both inside and outside. Shape: outside petal—broad lanceolate, nearly round, acute tip; intermediate—broad lanceolate with acute tip; inside—lanceolate with acute tip.
Color: newly opened flower from plant grown outdoors (September 1967), Visalia, Calif.
*Outside petal.*—Outside surface—Straw Yellow 604/1 lightly overlaid with red near tip; inside surface—Straw Yellow 604/1 near base shading into Straw Yellow 604/2 and lightly overlaid with red near tip.
*Intermediate petal.*—Outside surface—Straw Yellow 604/1 very lightly tipped with red; inside surface—Straw Yellow 604/1 lightly tipped red.
*Inside petal.*—Outside surface—Straw Yellow 604/1; inside surface—Straw Yellow 604/1.
*General color effect newly opened flower.*—Soft yellow with pink tips (outdoors); soft yellow with little or no pink on tips (in greenhouse). Three days open (outdoors)—yellow areas change to near white with pink or light red areas larger and deeper shade, giving effect of pink or light red flower.
*Behaviour.*—Spent petals drop clean.
*Flower longevity* (September 1967—outdoors)—4 to 5 days. Cut flowers at living room temperature—3 to 4 days.
Reproductive organs:
*Stamens.*—Moderate number, arranged regularly about pistils.
*Filament.*—Short, irregular length, yellow.
*Pollen.*—Moderate amount, yellow.
*Pistils.*—Medium length and number.
*Styles.*—Medium length, bunched, greenish white.
*Stigma.*—Greenish white.
*Ovaries.*—All enclosed in calyx.
*Hips.*—Usually none.
*Sepals.*—Permanent; spear shaped.
*Seeds.*—None.
Foliage:
*Leaves.*—Compound of five leaflets; often 7 leaflets; abundant; small; leathery, glossy, disease resistant.
*Leaflets.*—Shape—lanceolate; margin finely serrate. Color—medium green; new growth often tinted bronze. Rachis—medium strength; upper side grooved; underside sparsely to moderately thorny. Stipules—medium length and width; medium length points, turning outward at angle of about 45 degrees.
Growth:
*Habit.*—Dwarf; bushy; semi-climbing; much branched.
*Growth.*—Vigorous.
*Canes.*—Medium to heavy (for the type); slender.
*Main stems.*—Color—medium green. Thorns—occasional, often none. Prickles—none. Hairs—none.
*Branches.*—Color—medium green. Thorns—occasional, often one. Prickles—none. Hairs—none.
*New shoots.*—Color—medium green, often tinted bronze (outdoors). Thorns—few or none. Prickles—none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, much branched semi-climbing type, as illustrated and described, characterized by buds and flowers resembling the Peace rose (Pl. Patent 591—expired) in general form and coloring, the general color effect of the freshly opened flower being a yellow and pink blend; and further characterized by a plant of vigorous, compact growth which may be easily contained as a low bush or allowed to grow naturally into a semi-climber, easy to propagate by budding or from soft wood cuttings; with small medium green foliage, an abundance of bloom borne almost continuously throughout the growing season with flowers borne usually in small clusters.

No references cited

ROBERT E. BAGWILL, Primary Examiner